United States Patent
Ralph

(10) Patent No.: US 12,251,078 B2
(45) Date of Patent: Mar. 18, 2025

(54) SHEATH TIP WITH ANGLED DISTAL FACE

(71) Applicant: GYRUS ACMI, INC, Westborough, MA (US)

(72) Inventor: Christopher R. Ralph, Woodinville, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 382 days.

(21) Appl. No.: 15/936,081

(22) Filed: Mar. 26, 2018

(65) Prior Publication Data

US 2019/0290106 A1    Sep. 26, 2019

(51) Int. Cl.
*A61M 25/06*    (2006.01)
*A61B 1/00*    (2006.01)

(52) U.S. Cl.
CPC . *A61B 1/00135* (2013.01); *A61M 2025/0687* (2013.01); *A61M 2205/0216* (2013.01)

(58) Field of Classification Search
None
See application file for complete search history.

(56) References Cited

U.S. PATENT DOCUMENTS

| | | | | |
|---|---|---|---|---|
| 5,642,860 | A | * | 7/1997 | Bush ................... B05B 1/14 239/333 |
| 10,842,556 | B1 | * | 11/2020 | Tandri ................ A61B 18/1492 |
| 2001/0044606 | A1 | | 11/2001 | Inkpen et al. |
| 2005/0234347 | A1 | * | 10/2005 | Yamataka .......... A61B 1/00188 600/476 |
| 2007/0156116 | A1 | * | 7/2007 | Gonzalez .......... A61M 25/0136 604/528 |
| 2007/0249899 | A1 | * | 10/2007 | Seifert ............... A61B 1/00041 600/109 |
| 2008/0045859 | A1 | * | 2/2008 | Fritsch ............... A61B 17/3417 600/567 |

(Continued)

FOREIGN PATENT DOCUMENTS

| | | |
|---|---|---|
| CN | 103417184 | 12/2013 |
| CN | 103784195 | 5/2014 |

(Continued)

OTHER PUBLICATIONS

"United Kingdom Application Serial No. 1904075.7, Office Action mailed Oct. 7, 2021", 5 pgs.

(Continued)

*Primary Examiner* — Aurelie H Tu
(74) *Attorney, Agent, or Firm* — Schwegman Lundberg & Woessner, P.A.

(57) ABSTRACT

Disclosed embodiments include apparatuses, systems, and methods for providing a sheath tip with an angled distal face to conform the sheath to a surface of tissue toward which the sheath is being extended to potentially help reduce or avoid tissue damage upon extending a sheath to convey an elongated instrument for sampling or treatment. In an illustrative embodiment, an apparatus includes a sheath tip configured to be positioned at an end of a sheath that is extendable toward a tissue at an angle to a surface of the tissue. The sheath tip has a distal end that is angled such that a periphery of the sheath tip at the distal end is configured to generally conform to the surface of the tissue.

18 Claims, 7 Drawing Sheets

(56) References Cited

U.S. PATENT DOCUMENTS

| | | | |
|---|---|---|---|
| 2009/0204005 A1* | 8/2009 | Keast | A61B 1/018 604/164.01 |
| 2013/0225997 A1* | 8/2013 | Dillard | A61B 10/0283 600/439 |
| 2013/0317339 A1* | 11/2013 | Waldstreicher | A61B 18/1492 600/409 |
| 2013/0324985 A1 | 12/2013 | Whiteley | |
| 2014/0324098 A1 | 10/2014 | Hissong | |
| 2014/0378910 A1 | 12/2014 | Wong et al. | |
| 2016/0249784 A1* | 9/2016 | Bresco Torras | A61B 1/00165 600/128 |
| 2016/0367279 A1* | 12/2016 | Orphanos | A61B 18/148 |
| 2016/0374649 A1* | 12/2016 | Kramer | A61B 17/12013 600/567 |
| 2017/0112569 A1 | 4/2017 | Motosugi et al. | |
| 2017/0127917 A1 | 5/2017 | Cheng et al. | |

FOREIGN PATENT DOCUMENTS

| | | |
|---|---|---|
| CN | 106659486 | 5/2017 |
| CN | 106999172 | 8/2017 |
| CN | 110353613 A | 10/2019 |
| DE | 102019106176 A1 | 9/2019 |
| GB | 2573640 A | 11/2019 |
| GB | 2573640 B | 10/2022 |
| JP | 2010263926 A | 11/2010 |
| JP | 2019171058 A | 10/2019 |
| JP | 7396805 B2 | 12/2023 |
| WO | WO-2009131583 A1 * 10/2009 ........ A61M 25/0068 |
| WO | WO-2016143204 A1 | 9/2016 |

OTHER PUBLICATIONS

"United Kingdom Application Serial No. 1904075.7, Response filed Dec. 7, 2021 to Office Action mailed Oct. 7, 2021", 7 pgs.

"United Kingdom Application Serial No. 1904075.7, Search Report mailed Sep. 9, 2019", 4 pgs.

"Japanese Application Serial No. 2019-056520, Notification of Reasons for Refusal mailed Mar. 6, 2023", w/ English translation, 12 pgs.

"Japanese Application Serial No. 2019-056520, Notification of Reasons for Rejection mailed Jul. 10, 2023", W English Translation, 4 pgs.

"Japanese Application Serial No. 2019-056520, Response filed Aug. 24, 2023 to Notification of Reasons for Rejection mailed Jul. 10, 2023", with English claims, 6 pgs.

"Chinese Application Serial No. 201910231839.9, Office Action mailed Sep. 2, 2023", W English Translation, 13 pgs.

"Japanese Application Serial No. 2019-056520, Response filed Jun. 5, 2023 to Notification of Reasons for Refusal mailed Mar. 6, 2023", w/ english claims, 7 pgs.

"Chinese Application Serial No. 201910231839.9, Response filed Jan. 5, 2024 to Office Action mailed Sep. 2, 2023", w/ english claims, 14 pgs.

"Chinese Application Serial No. 201910231839.9, Office Action mailed Apr. 10, 2024", w English translation, 10 pgs.

"Chinese Application Serial No. 201910231839.9, Response filed May 29, 2024 to Office Action mailed Apr. 10, 2024", W English Claims, 11 pgs.

"Chinese Application Serial No. 201910231839.9, Decision of Rejection mailed Jul. 5, 2024", w machine translation, 13 pgs.

"Chinese Application Serial No. 201910231839.9, Request for Reexamination filed Sep. 30, 2024", w current English claims, 11 pgs.

* cited by examiner

SHEATH TIP WITH ANGLED DISTAL FACE

FIELD

The present disclosure relates to a sheath used to extend an elongated instrument.

BACKGROUND

The statements in this section merely provide background information related to the present disclosure and may not constitute prior art.

The ability to access tissue within a patient's body without invasive surgery allows for ever-improving types of analysis, diagnosis, and treatment with reduced pain, reduced recovery time, and a reduced risk of complications. By way of two examples, endoscopic and catherization techniques have enabled evaluation and treatment of numerous internal lesions without invasive surgery.

For example, suspected or actual lesions may be sampled or treated by extending an elongated medical instrument, such as a sampling needle, through a sheath that is positioned by an insertion control system, such as a bronchoscope or an endoscope. The sheath may be extended from the insertion control system to position the elongated medical instrument, then the elongated instrument itself may be deployed for sampling or treatment.

Use of the insertion control system, while possibly avoiding invasive surgery, may pose its own challenges. For example, because the insertion control system may operate in tight spaces, it may be a challenge to engage in sampling or treatment at a desired position within in a body while minimizing or attempting to avoid or minimize trauma to the tissue at or near the desired position or other undesirable effects resulting from contact between the insertion control system and tissue walls.

SUMMARY

Disclosed embodiments include apparatuses, systems, and methods for providing a sheath tip with an angled distal face to conform the sheath to a surface of tissue toward which the sheath is being extended. It will be appreciated that various disclosed embodiments seek to help reduce or avoid tissue damage upon a sheath being extended to convey an elongated instrument for sampling or treatment or other undesirable effects resulting from the sheath pushing against tissue surfaces.

In an illustrative embodiment, an apparatus includes a sheath tip configured to be positioned at an end of a sheath that is extendable toward a tissue at an angle to a surface of the tissue. The sheath tip has a distal end that is angled such that a periphery of the sheath tip at the distal end is configured to generally conform to the surface of the tissue.

In another illustrative embodiment, a system includes a sheath defining therein a lumen and that is configured to be extendable toward a tissue at an angle to a surface of the tissue. An elongated medical instrument is configured to be delivered through the lumen in the sheath. An insertion control system is configured to convey the sheath to a desired location within a body. An instrument control system is configured to direct operation of the elongated medial instrument when the elongated medical instrument reaches a desired position. A sheath tip is configured to be positioned at an end of the sheath. The sheath tip has a distal end that is angled such that a periphery of the sheath tip at the distal end is configured to generally conform to the surface of the tissue.

In a further illustrative embodiment, a method includes preparing an elongated instrument for being conveyed into a body through a lumen in a sheath. The sheath is to be extended toward a tissue at an angle to a surface of the tissue. The sheath includes a sheath tip at a distal end of the sheath, with a distal end of the sheath tip being angled such that a periphery of the sheath tip at the distal end is configured to generally conform to the surface of the tissue. The sheath conveying the elongated instrument into the body is inserted into the body.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings.

DETAILED DESCRIPTION

The following description is merely illustrative in nature and is not intended to limit the present disclosure, application, or uses. It will be noted that the first digit of the three-digit reference numbers corresponds to the number of the figure in which the element first appears.

The following description explains, by way of illustration only and not of limitation, various embodiments of sheath tips to help reduce or seek to prevent undesirable effects resulting from extension of a sheath toward a surface, as well as systems including such sheath tips and methods of using the same. As will be described in detail below, in various illustrative embodiments the sheath tips are configured to have a shape that generally conforms to a tissue surface toward which the sheath tip is extended, thereby potentially helping to avoid or lessen displacement of instruments from tissue walls or trauma to the tissue surface.

Figure 1:
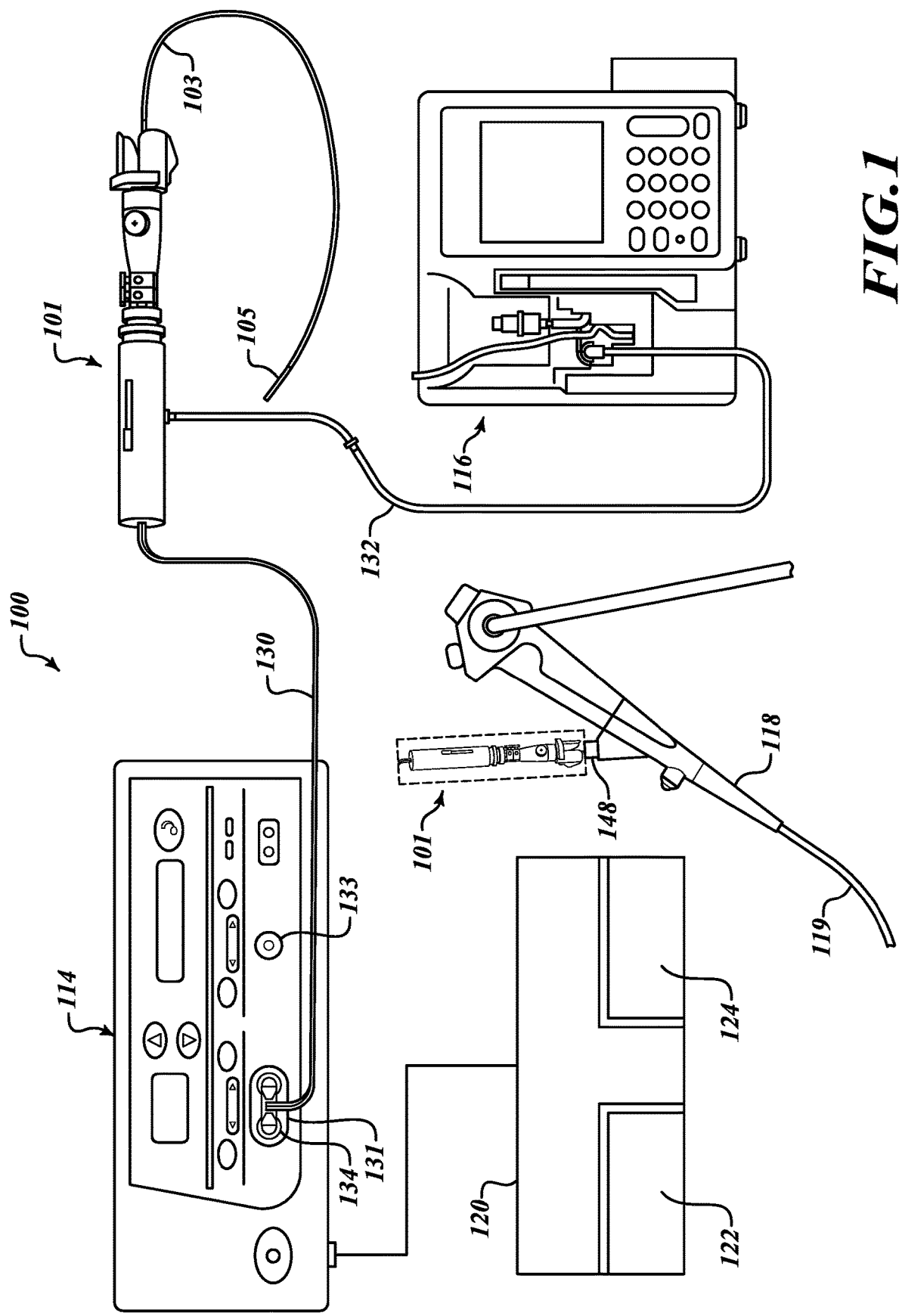
FIG. 1 is a block diagram in partial schematic form of an illustrative system for sampling or treating tissue.

Referring to FIG. 1, in various embodiments, an illustrative system 100 is provided for sampling or treating tissue at a reference point in an anatomical region of a patient (not shown in FIG. 1). For one example, the system 100 may include a sampling device with a vacuum system for drawing a sample via a sampling needle. Alternatively, the system 100 may be a bipolar radio frequency (RF) system, as desired, for using electrical current to ablate or coagulate tissue in a patient. Further alternatively, the system 100 may include a mechanical or laser-based cutting system for incising tissue in a patient. Any such system may involve insertion of an elongated instrument into a patient to perform a desired procedure, and any such elongated instrument may be inserted into a patient via a sheath which may desirably end in a sheath tip as disclosed herein.

In some embodiments, the system 100 includes an elongated medical instrument controllable by a user interface 101, one or more instrument control systems 114 and 116, an insertion control system 118, and various supporting apparatuses. The user interface 101 may include a positioning device for positioning a distal end 113 of a sheath 103 relative to a position of interest in a body (not shown). The user interface 101 also may be configured to direct a position of an elongated instrument (not shown) that is housed within the sheath 103. The elongated instrument, for example, may include a sampling needle, as described below with reference to FIGS. 4-6, one or more electrodes, an imaging device, a probe, a cutting device, or any other elongated device. The one or more control systems 114 and 116 may be coupled to the elongated instrument and include devices to draw fluid or tissue, provide electrical current, provide fluid, monitor sensor data, or to perform other functions.

The insertion control system 118 may include a bronchoscope, an endoscope, or another insertion system configured to maneuver an insertion device 119 that may be equipped with a steering mechanism as well as optical, ultrasound, or other sensors to monitor the course of the insertion device 119. The user interface 101 may be received into the insertion control system 118 so that the insertion control system 118 at a port 148 for the insertion control system 118 so that the insertion control system 118 may direct the insertion device 119 to convey the distal end 113 of the sheath 103 to a desired location in a body where the user interface 101 then may be used to manipulate an associated elongated instrument to perform a desired function.

The system may represent any number of sampling or treatment systems. For one example, the system 100 may be a sampling system to collect a tissue sample using a sampling needle, such as described further below with reference to FIGS. 4-6. In such case, the insertion control system 118 may include a bronchoscope if the sample is to be collected from a respiratory system or an endoscope if the sample is to be collected from a digestive system. One instrument control system 114 may be used to receive and process sensor data and be operated by controls 120, 122, and 124. Another instrument control system 116 may be a pump or other vacuum source to draw a tissue or fluid sample from the sampling needle that may extend from the distal end 113 of the sheath 103.

For another example, the system 100 may be a cutting system for cutting through a tissue obstruction. In such case, the insertion control system 118 may include an endoscope to direct the if the sample is to be collected from a digestive system. One instrument control system 114 may be used to receive and process sensor data and be operated by controls 120, 122, and 124. Another instrument control system 116 may be a cutting control system to motivate a reciprocating and/or rotating cutting apparatus extending from the distal end 113 of the sheath 103.

For still another example, the system 100 may be an electrosurgical radio frequency (RF) system for ablating, cauterizing, or coagulating tissue. In such case, the insertion control system 118 may include a bronchoscope if the sample is to be collected from a respiratory system or an endoscope if the sample is to be collected from a digestive system. One instrument control system 114 may be a generator operating as a switchable power source 114 to apply electrical power to an elongated instrument extending from the distal end 113 of the sheath. The user interface 101 electrically communicates with the switchable power source 114 though an electrical conductor 130. In some embodiments, the electrical conductor 130 is connected to an outlet 131 when the system is operated in a bipolar mode. The electrical conductor 130 may be coupled with the outlet 131 using an electrical connector 134 configured to electrically engage the outlet 131. The switchable power source 114 can be operated with the use of a foot operated unit 120 electrically connected to the switchable power source 114. The foot operated unit 120 may include, for example, a pedal 122 that instructs the switchable power source 114 to apply electrical power to electrode(s) (described below) to cut and/or ablate tissue and a pedal 124 that instructs the generator 114 to apply a lower quantity of electrical power to the electrode(s) to coagulate tissue.

The user interface 101 is further connected to the conductive fluid source 116 with a tube 132 that facilitates the flow of liquid, for example saline solution or another conductive fluid, from the conductive fluid source 116 to the user interface 101. Another instrument control system 116 may be a conductive fluid source 116, such as an infusion pump controllable by a switch, to provide a conductive fluid to the distal end 113 of the sheath 103, where the conductive fluid may be vaporized by applied electrical power to generate heat to ablate or cauterize tissue.

The system 100 may include any number of medical systems or non-medical systems in which an elongated instrument is extended via a sheath 103 to perform an operation, and sheath tips in accordance with the present disclosure may be applied to the distal end 113 of the sheath 103 to facilitate such operations. Embodiments of the sheath tips of the present disclosure are not limited to use with any particular systems or functions. Any applications for use of the sheath tips of the present disclosure are provided solely for illustration and should not be taken as limiting.

Figure 2:
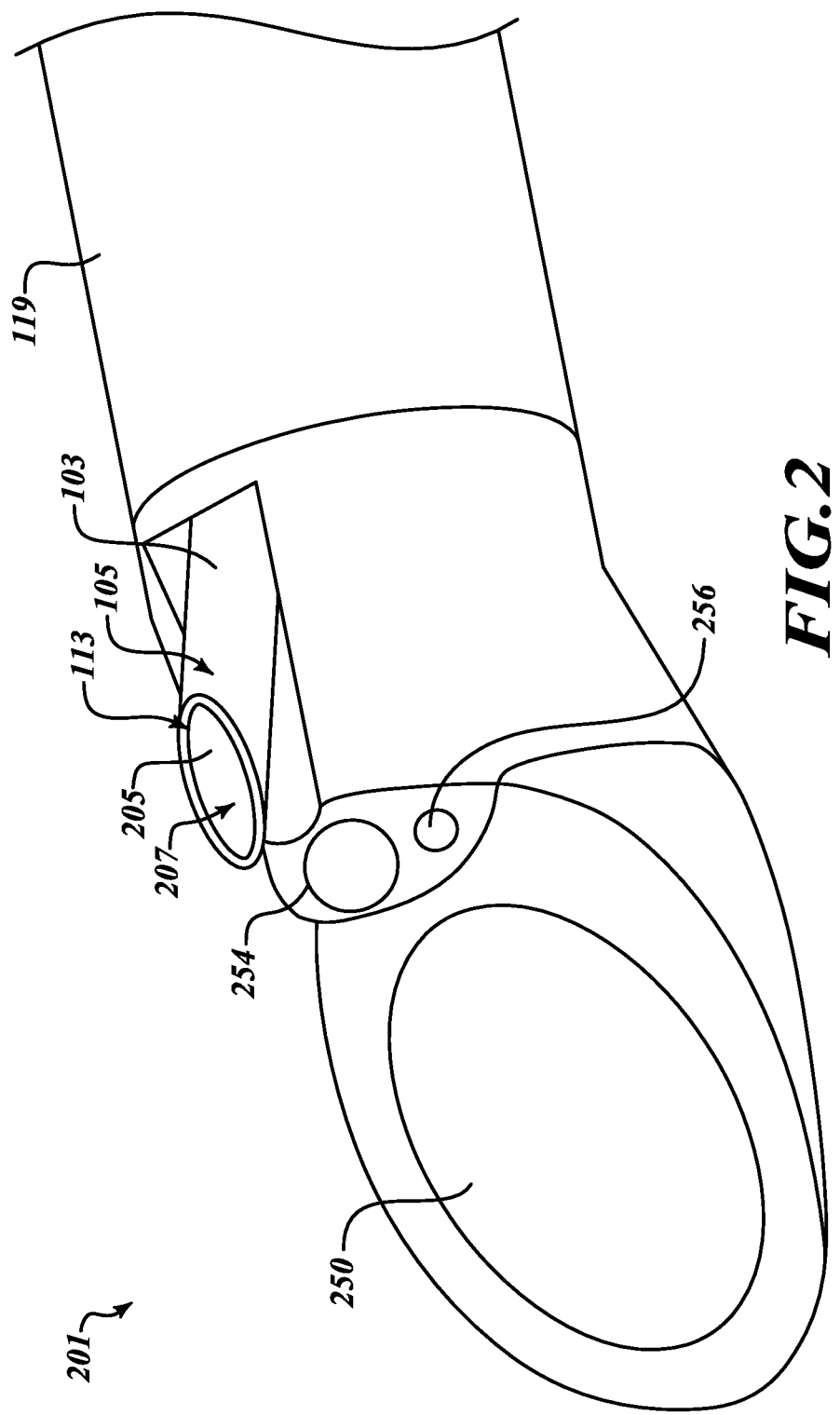
FIG. 2 is a perspective view of a head on an insertion device including a sheath fitted with an illustrative sheath tip having an angled distal face.

Referring to FIG. 2, a head 201 of the insertion device 119 includes various sensor devices or related devices 250, 254, and 256 usable in positioning the distal end 113 of the sheath 103 (FIG. 1). For example, the head 201 may support an ultrasound transducer 250 that emits ultrasound energy and receives reflected ultrasound energy. The head 201 also may support a camera 254, for which a light source 256 may be provided to illuminate a region adjacent the head 201. The ultrasound transducer 250 and/or the camera 254 may be used to identify lesions or other regions of interest to be sampled or treated by an elongated instrument (not shown in FIG. 2) to be conveyed through the sheath 103.

The distal end 113 of the sheath 103 defines therein a lumen 207 from which the elongated instrument (not shown in FIG. 2) may extend. The distal end 113 of the sheath may be fitted with an embodiment of an angled sheath tip 205. Specifically, the angled sheath tip 205 has an angled distal face that is shaped around a periphery 209 of the angled sheath tip 205 so as to generally conform to the surface of a tissue to which the sheath 103 is to be extended, as further described below.

Figure 3A:
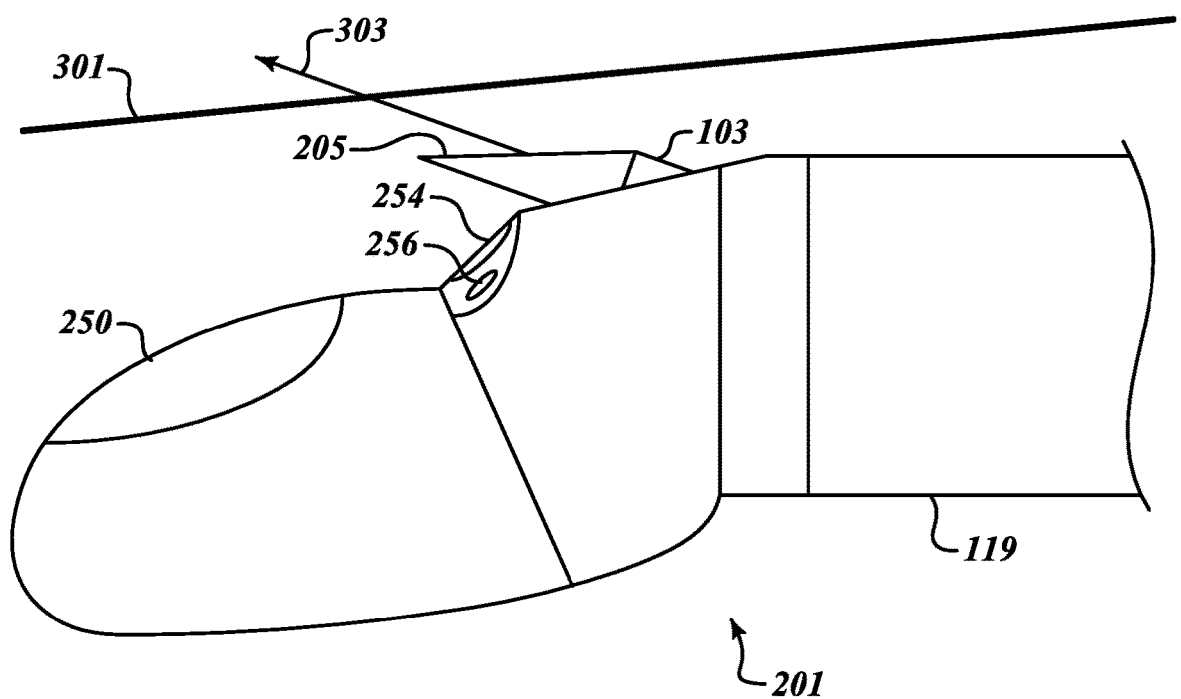
FIGS. 3A and 3B are side views of the head of the insertion device of FIG. 2 in preparation for extension of the sheath and following extension of the sheath having an illustrative sheath tip having an angled distal face.

Referring to FIG. 3A, the head 201 is disposed adjacent a tissue surface 301, such as an interior surface of a bodily tract into which the head 201 may be inserted. The head 201 is in position for extension of the sheath 103 before the sheath 103 is extended. When deployed, the sheath 103 will extend along an axis 303. However, the angled sheath tip 205 disposed at the distal end 113 of the sheath 103 may help reduce or avoid unnecessary or unwanted impact between the sheath 103 and the tissue surface 301 as described below with reference to FIG. 3B.

Figure 3B:
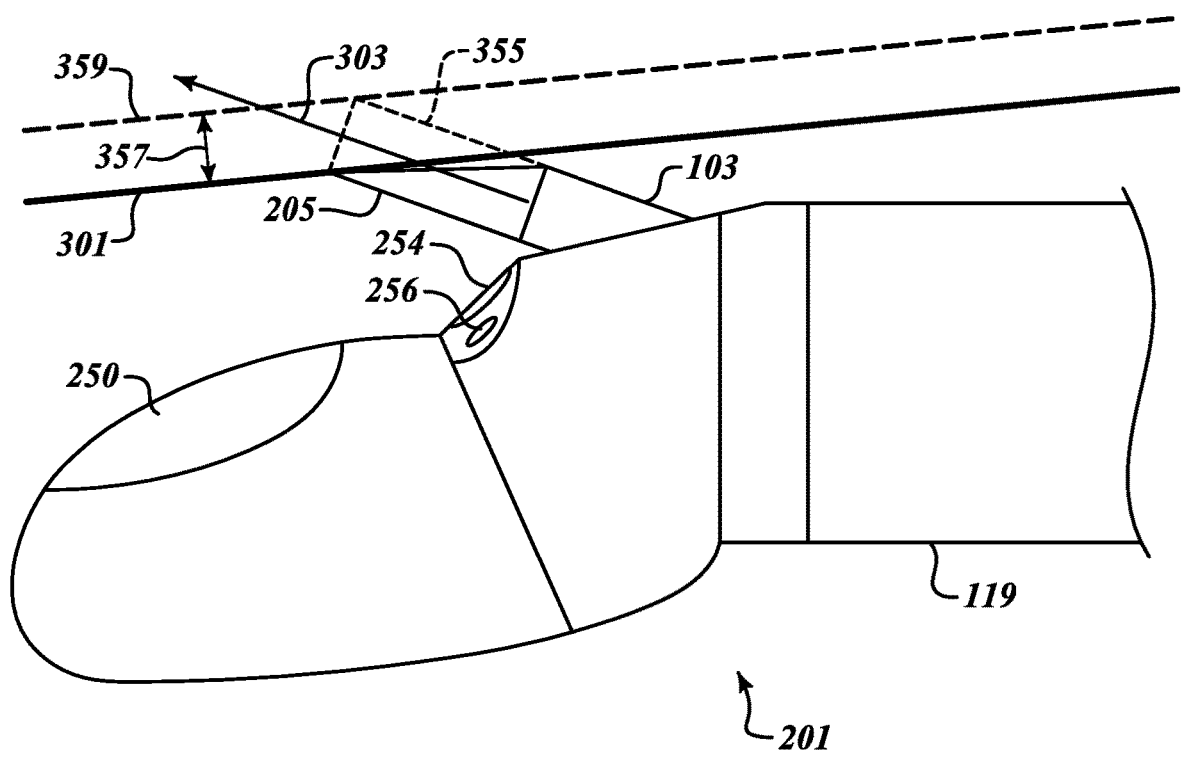

Referring to FIG. 3B, after extending the sheath 103, the angled sheath tip 205 generally conforms to the tissue surface 301. Without the angled sheath tip 205, the sheath 103 may potentially intersect the tissue wall 301. A projection 355 represented by a dashed line about the axis 303 shows that extending the sheath 103 without the angled sheath tip 205 potentially might have impinged upon the tissue surface 301. Extending the sheath 103 without the angled sheath tip 205 may have undesirable effects. For one example, the extension of the sheath 103 against the tissue wall 301 may displace the head 201 from the tissue wall 301, moving the tissue wall 301 away a relative distance 357 to a new wall location represented by dotted line 359. (It will be appreciated that the relative displacement of the head 201 from the tissue wall 301 may be as a result of movement of the head 201 away from the tissue wall 301, movement of the tissue wall 301 from the head 201, or some combination of movement of the head 201 and the tissue wall 301.) Such displacement may, therefore, displace the ultrasound transducer 250 from the tissue wall 301 and impair the ability of the ultrasound transducer 250 to scan tissues at or behind the tissue wall 301. For another example, extension of the sheath 103 without the angled sheath tip 205 may distend or traumatize tissue at the tissue wall 301. Instead of the sheath 103 potentially displacing, distending, or traumatizing the tissue surface 301 upon being extended along the axis 303 against the tissue surface 301, the angled sheath tip 205 is shaped to generally conform to the tissue surface 301 to prevent potential undesirable effects from extension of the sheath 103.

Figure 4:
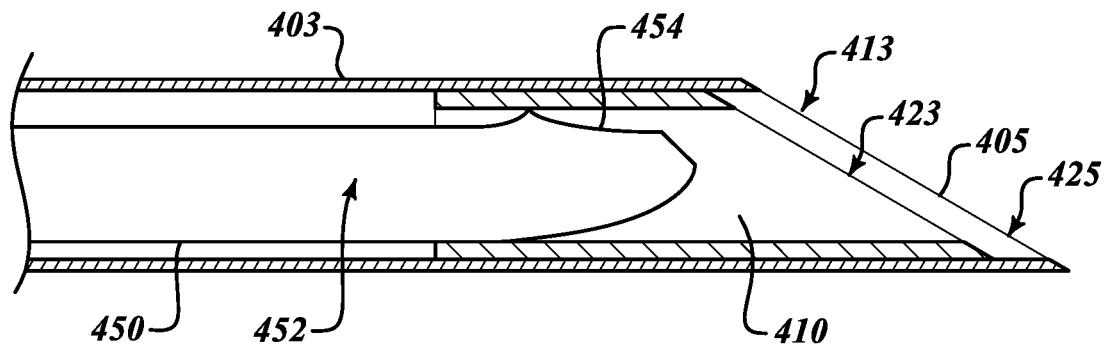
FIGS. 4 and 5 are cutaway views of an end of a sheath configured with a sheath tip having an angled distal face.
Figure 5:
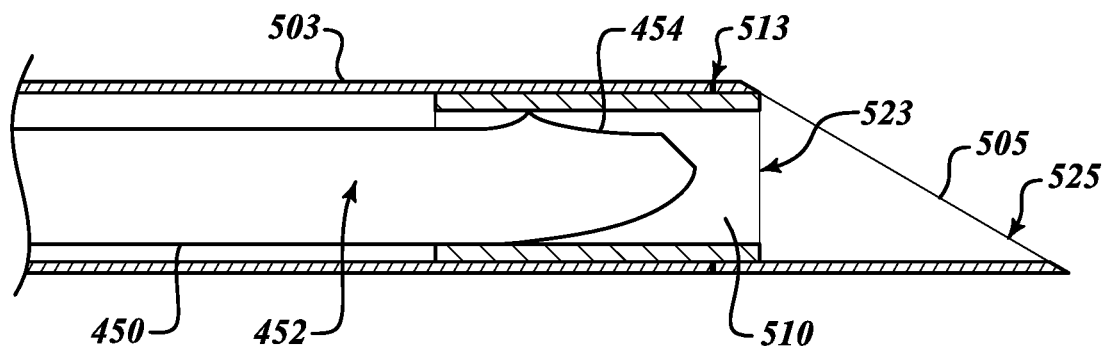

FIGS. 4 and 5 show different illustrative angled sheath tips 405 and 505. Referring to FIG. 4, an elongated instrument 450 is housed in a sheath 403. The elongated instrument 450 is a sampling needle configured to draw a tissue sample from a tissue surface, lesion, or other body, and it includes an interior lumen 452 that terminates in an open sampling end 454. The elongated instrument 450 may be extended from the sheath 403 to collect a sample of tissue (not shown) at the open sampling end 454 that is then drawn through the lumen 452 by a vacuum source for collection and testing. As described in detail with reference to FIG. 1, however, it should be understood that the elongated instrument 450 may include any of a number of instruments including electrodes, cutting devices, other apparatuses, and the sampling needle shown is used here only by way of illustration and not limitation.

The angled sheath tip 405 of FIG. 4 is integrally formed with the sheath 403 at a distal end 413 of the sheath 403. The angled sheath tip 405 may be molded, extruded, or otherwise formed as part of the sheath 403 when the sheath 403 is formed. The angled sheath tip 405 also may be formed by cutting away a portion of the sheath 403 at the distal end 413 to form the angled sheath tip 405 The sheath 403 and the angled sheath tip 405 may be formed of plastic or any other flexible material. The angled sheath tip 405 has an angled distal end 425, as previously described, so as to generally conform with a surface toward which the sheath 403 and the angled sheath tip 405 are extended.

In addition, the sheath 403 may be fitted with an insert 410 that is insertable or otherwise receivable within the sheath 403. The insert may serve the purpose of stiffening the sheath 403 short of the distal end 413 for purposes of assisting extension of the sheath 403 through the insertion device 119 and the head 201 (FIGS. 1, 2, 3A, and 3B). The insert 410 also may protect the sheath 403 from potential damage that may be caused by the elongated instrument 450, such as might be caused by a potentially sharp open sampling end 454 of a sampling needle while the sheath 403 and/or the insertion device 119 are maneuvered to a desired location within a body (not shown). The insert 410 may be received within the distal end 413 of the sheath 403 just inside the angled sheath tip 405. As shown in FIG. 4, the insert 410 may have an angled distal end 423 such that the angled distal end 423 of the insert 410 is generally parallel with the angled distal end 425 of the angled sheath tip 405.

Referring to FIG. 5, a separately formed angled sheath tip 505 is joined to a distal end 513 of a sheath 503. In such embodiments, the angled sheath tip 505 may be molded, extruded, or otherwise separately formed from the sheath 503. The angled sheath tip 505 may be formed of plastic or any other suitable flexible material. The angled sheath tip 505 may be joined to the distal end 513 of the sheath 503 by adhesives, heat welding, or any other technique that is operable to join together the materials that comprise the sheath 503 and the angled sheath tip 505.

Also, and comparable to the illustrative embodiment of FIG. 4, the sheath 503 may be fitted with an insert 510 that is insertable or otherwise receivable within the sheath 503. The insert may serve the purpose of stiffening the sheath 503 short of the distal end 513 for purposes of assisting extension of the sheath 503 through the insertion device 119 or protecting the sheath 503 from potential damage that may be caused by the elongated instrument 450, as described with reference to FIG. 4. The elongated instrument 450, in the form of a sampling needle, is shown in FIG. 5 by way of illustration and not limitation, as in FIG. 4. The insert 510 may be received at the distal end 513 of the sheath 503. A distal end 523 of the insert may not be angled like a distal end 525 of the angled sheath tip 505. Instead, the distal end 523 of the insert 510 may be generally parallel with the distal end 513 of the sheath 503. The insert 510 may be situated where the angled sheath tip 505 meets the distal end 513 of the sheath 503, potentially providing support to a joint where the angled sheath tip 505 is joined to the distal end 513 of the sheath 503.

It should be noted that the insert 410 (that has the angled distal end 423) (FIG. 4) may be used with the angled sheath tip 505 that is formed separately from the sheath 503, as described with reference to FIG. 5. On the other hand, the insert 510 (that has the distal end 523 that is not angled) (FIG. 5) may be used with the angled sheath tip 405 that is integrally formed with the sheath 403, as described with reference to FIG. 4. The present disclosure is not limited to the specific configurations of components literally shown in the figures, and elements shown in one illustrative embodiment may be combined with elements shown in other illustrative embodiments.

Figure 6:
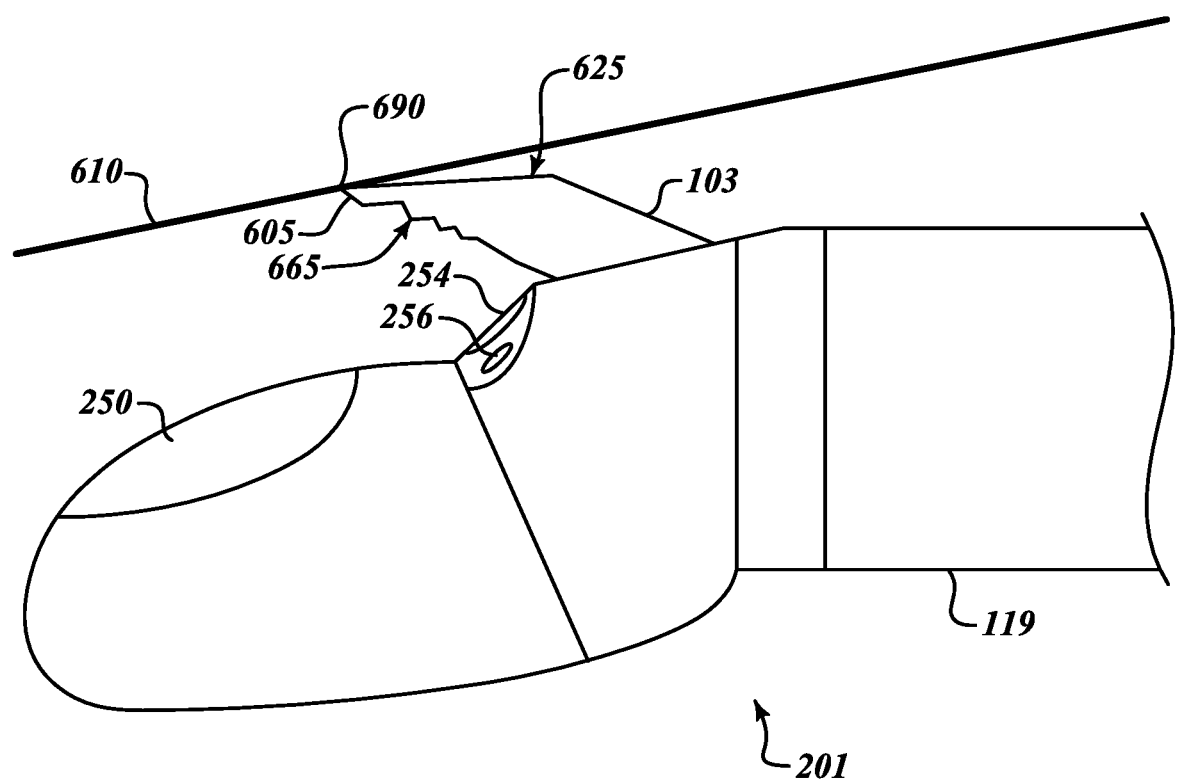
FIG. 6 is a side view of the head of the insertion device of FIG. 2 where the sheath includes an illustrative sheath tip having a deformable angled distal face.

Referring to FIG. 6, it may be desirable to form an angled sheath tip 605 that is both angled and deformable. Although the angled sheath tip 605 is shaped to conform to conform with a tissue surface 610 against which the angled sheath tip 605 may be extended, the angled sheath tip 605 may nonetheless impact the tissue wall at a contact point 690 where the tissue surface 610 may potentially incur some trauma from impact with the angled sheath tip 605, or extension of the angled sheath tip 605 may result in relative displacement of the head 201 from the tissue wall 610, as previously described with reference to FIG. 3B. The angled sheath tip 605 thus may be formed to permit deformation 665 to absorb strain that may otherwise may potentially result in trauma from contact between the angled sheath tip 605 and the tissue surface 610.

Figure 7A:
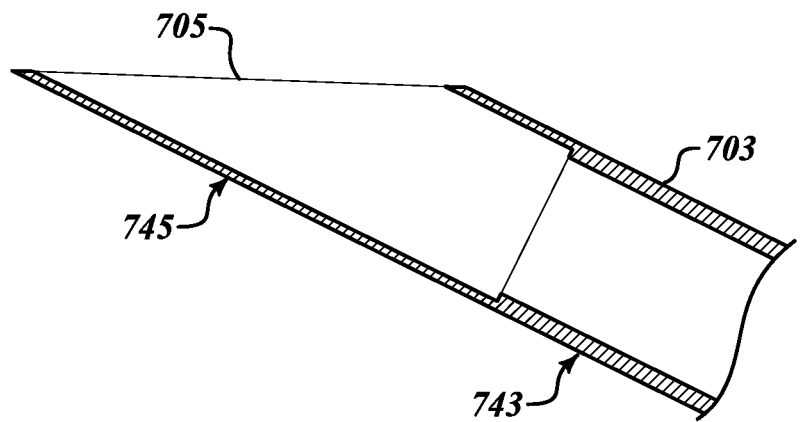
FIGS. 7A and 7B are side views of illustrative sheath tips having deformable angled distal faces.
Figure 7B:
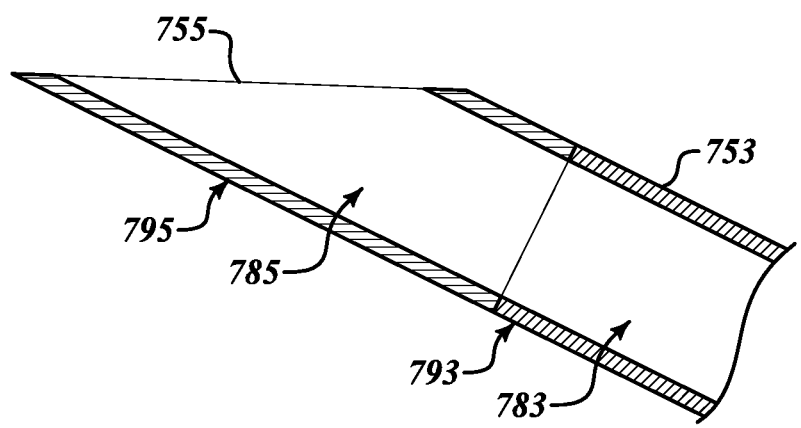

In providing for a degree of deformability and referring to FIGS. 7A and 7B, angled sheath tips 705 and 755, respectively, each may include a construction different from that of the sheaths 703 and 753, respectively, from which each angled sheath tip extends. Referring to FIG. 7A, the angled sheath tip 705 may be formed of a same material as the sheath 703 but may have a different wall thickness than the sheath 703. The angled sheath tip 705 may be formed along with the sheath 703, or the angled sheath tip 705 may be formed separately from the sheath 703 and then joined with the sheath, as previously described with reference to FIGS. 4 and 5. A wall thickness 745 of the angled sheath tip 705 may be different than a wall thickness 743 of the sheath 703. For example, the wall thickness 745 of the angled sheath tip 705 may be thinner than that of the wall thickness 743 of the sheath 703. As a result, even if the angled sheath tip 705 is comprised of a same material as the sheath 703, the angled sheath tip 705 may be more deformable than the sheath 703.

Referring to FIG. 7B, the angled sheath tip 755 may be comprised of a material 785 that is different than a material 783 of which the sheath 773 is comprised. The material 785 of the angled sheath tip 755 may be more pliable or deformable than that of a material 783 used in forming the sheath 753, thereby rendering the angled sheath tip 755 more deformable than the sheath 753. A wall thickness 795 of the angled sheath tip 755 may be the same or different from a wall thickness 793 of the sheath 753. A combination of different materials and/or different wall thicknesses may be combined to present an angled sheath tip having a desired degree of deformability to, along with the shaping of the angled sheath tip, potentially help reduce or prevent impact trauma or unwanted displacement between instruments and the tissue wall, as previously described with reference to FIG. 3B.

Figure 8:
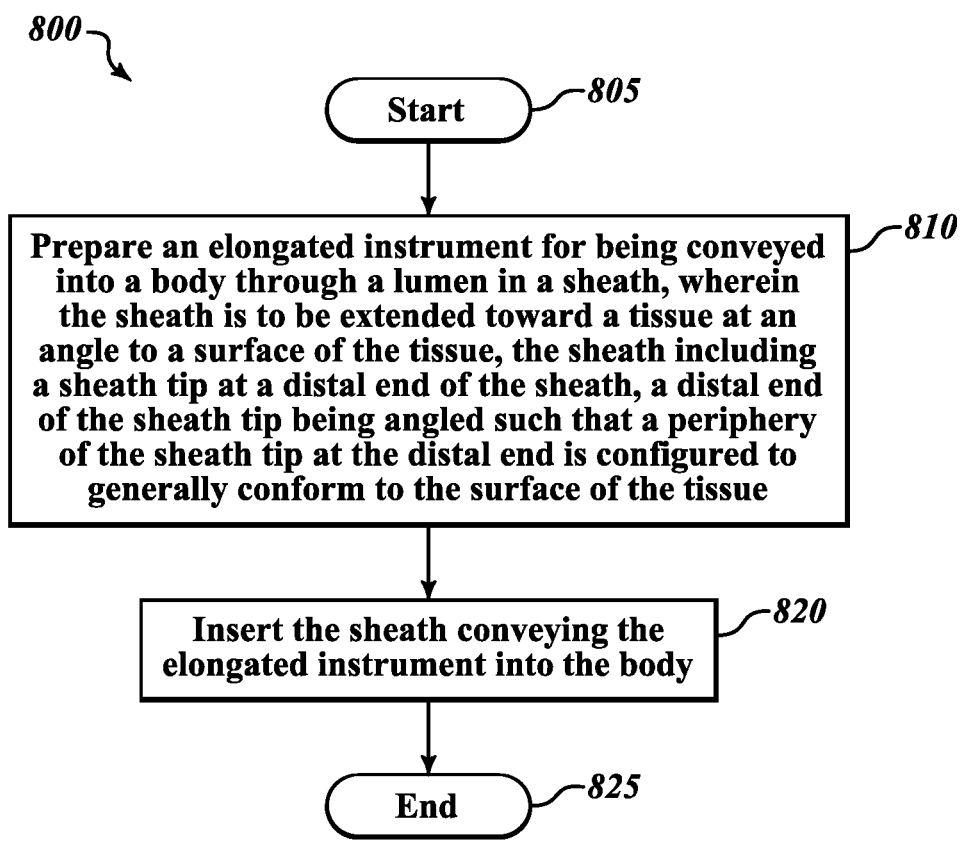
FIG. 8 is a flow diagram of an illustrative method of operating an apparatus equipped with a sheath tip.

Referring to FIG. 8 an illustrative method 800 of using a sheath tip in deploying an elongated instrument via a sheath is provided. The method 800 starts at a block 805. At a block 810, an elongated instrument is prepared for being conveyed into a body through a lumen in a sheath, wherein the sheath is to be extended toward a tissue at an angle to a surface of the tissue. The sheath includes a sheath tip at a distal end of the sheath where a distal end of the sheath tip is angled such that a periphery of the sheath tip at the distal end is configured to generally conform to the surface of the tissue toward which the sheath is extendable. Preparation for using the elongated instrument may include, for example, inserting a sheath housing an elongated instrument into an insertion system, maneuvering the insertion system to a desired location in a body, or other steps that logically may proceed deploying or using the elongated instrument. The configuration of angled sheath tips useable in accordance with the illustrative method 800 are described with reference to FIGS. 2, 3A, 3B, 4, 5, 6, 7A, and 7B.

At a block 820, the sheath conveying the elongated instrument is inserted into the body. The insertion of the elongated instrument is described with reference to FIGS. 1, 2, 3A, 3B, 4, 5, and 6. The method 800 ends at a block 825.

It will be appreciated that the present descriptions of the sheath tips being used in the insertion of elongated instruments into a body via a sheath are not limiting to either the types of elongated instruments described or to use with medical instruments in a biological body. Sheath tips in the nature of those described could be used in any application where a lumen may contact a surface to which damage could result from impact of the lumen against the surface.

It will also be appreciated that the detailed description set forth above is merely illustrative in nature and variations that do not depart from the gist and/or spirit of the claimed subject matter are intended to be within the scope of the claims. Such variations are not to be regarded as a departure from the spirit and scope of the claimed subject matter.

What is claimed is:

1. An apparatus comprising:
   an insertion device including an ultrasound transducer disposed on a distal end and a camera;
   a sheath defining therein a lumen, the sheath deliverable through the insertion device to a target location and extendable out of the insertion device along a sheath extension axis that extends from a sidewall of the insertion device to direct the sheath towards a tissue at the target location;
   a sampling needle having a sharp open end and receivable within the lumen to be delivered through the lumen in the sheath to the target location, wherein the sheath extension axis is angled relative to a longitudinal axis of the insertion device to direct the sampling needle to enter the tissue at the target location in front of the ultrasound transducer when the sampling needle is extended from the insertion device along the extension axis;
   a sheath tip disposed at an end of the sheath, the sheath tip having a distal end that is angled at a non-perpendicular angle with respect to the extension axis such that a periphery of the sheath tip at the distal end conforms to the a surface of the tissue at the target location upon extension along the extension axis from the insertion device towards the tissue at the target location; and
   a stiffening insert disposed within the sheath tip inside the periphery of the sheath tip at the distal end to protect the periphery of the sheath tip at the distal end from the sharp open end of the sampling needle upon delivery of the sampling needle out of the sheath tip to draw a tissue sample from the tissue at the target location,
   wherein the camera is positioned proximal of the ultrasound transducer and distal of a side exit port in the sidewall of the insertion device.

2. The apparatus of claim 1, wherein the sheath defines the lumen configured to extend an elongated medical device toward the surface of the tissue at the target location and the sheath tip defines an extension of the lumen toward the distal end of the sheath tip.

3. The apparatus of claim 1, wherein the sheath tip is an integral section of the sheath, the sheath tip being disposed at the end of the sheath.

4. The apparatus of claim 1, wherein the sheath tip is a separate structure configured to be attached to the end of the sheath.

5. The apparatus of claim 4, wherein the sheath tip is configured to be physically coupled to the end of the sheath at a sheath insert that is receivable within the lumen of the sheath.

6. The apparatus of claim 1, wherein the sheath tip has at least one characteristic chosen from a first thickness that is less than a second thickness of the sheath and a first rigidity that is less than a second rigidity of the sheath.

7. The apparatus of claim 1, wherein the extension axis diverges away from the ultrasound transducer and intersects with the tissue at the target location.

8. The apparatus of claim 1, wherein a distal end of the stiffening insert that faces the distal end of the sheath tip is angled parallel with the distal end of the sheath tip.

9. The apparatus of claim 1, wherein the insertion device includes a light source to illuminate a region of tissue for imaging by the camera.

10. A system comprising:
a sheath defining therein a lumen and configured to be extendable along a sheath extension axis that diverges away from a longitudinal axis of an insertion control system to direct the sheath towards a tissue at a target location;
an ultrasound transducer disposed on a distal end of the insertion control system;
a camera disposed proximal of the ultrasound transducer and distal of a side exit port in the sidewall of the sheath;
a sampling needle having a sharp end configured to be delivered through the lumen in the sheath;
the insertion control system configured to convey the sheath to a desired location within a body and expel the sheath via an extension port along a sidewall of the insertion control system, the extension port directs the sheath along the sheath extension axis to enable extension of the sampling needle into the tissue along the sheath extension axis;
a sheath tip disposed at an end of the sheath, the sheath tip having a distal end that is angled at a non-perpendicular angle with respect to the extension axis such that a periphery of the sheath tip at the distal end conforms to a surface of the tissue at the target location upon extension along the extension axis from the insertion control system towards the tissue at the target location and the periphery of the sheath tip at the distal end is configured to deform upon contact with the surface of the tissue at the target location; and
a stiffening insert disposed inside the sheath tip rearward of the periphery of the sheath tip at the distal end to protect the periphery from the sharp end of the sampling needle upon delivery of the sampling needle out of the sheath tip, wherein the stiffening insert is configured to stiffen the sheath tip rearward of the periphery of the sheath tip at the distal end to prevent the sharp end of the sampling needle from impacting the sheath tip without preventing the periphery of the sheath tip at the distal end from deforming upon contact with the surface of the tissue at the target location.

11. The system of claim 10, wherein the sharp end of the sampling needle is configured to draw a tissue sample from the surface of the tissue at the target location.

12. The system of claim 10, wherein the sheath tip is an integral section of the sheath, the sheath tip being disposed at the end of the sheath.

13. The system of claim 10, wherein the sheath tip is a separate structure configured to be attached to the end of the sheath.

14. The system of claim 13, wherein the sheath tip is configured to be physically coupled to the end of the sheath at a sheath insert that is receivable within the lumen of the sheath.

15. The system of claim 10, wherein a distal end of the stiffening insert that faces the distal end of the sheath tip is angled parallel with the distal end of the sheath tip.

16. The system of claim 10, wherein the sheath tip has at least one characteristic chosen from a first thickness that is less than a second thickness of the sheath and a first rigidity that is less than a second rigidity of the sheath.

17. The system of claim 10, wherein the insertion control system is configured to extend the sheath at an oblique angle to the surface of the tissue at the target location and the periphery of the sheath tip at the distal end is oriented to conforms to the surface of the tissue at the target location.

18. An apparatus comprising:
an insertion device including an ultrasound transducer disposed on a distal end and a camera;
a sheath defining therein a lumen, the sheath deliverable through the insertion device to a target location and extendable out of the insertion device along a sheath extension axis that extends from a side exit port of the insertion device to direct the sheath towards a tissue at the target location;
a sampling needle having a sharp open end and receivable within the lumen to be delivered through the lumen in the sheath to the target location, wherein the sheath extension axis is angled relative to a longitudinal axis of the insertion device to direct the sampling needle to enter the target tissue in front of the ultrasound transducer when the sampling needle is extended from the insertion device along the extension axis; and
a sheath tip disposed at an end of the sheath, the sheath tip including an angled distal face that is parallel or flush with an outer profile of the insertion device and adjacent to the side exit port upon initial exit from the side exit port,
wherein the camera is positioned superior to and proximal of the ultrasound transducer and inferior to and distal of the side exit port for the sheath.

* * * * *